United States Patent
Yuyama et al.

(10) Patent No.: US 8,209,943 B2
(45) Date of Patent: Jul. 3, 2012

(54) DISTRIBUTED MEDICINE SUPPLYING DEVICE AND MEDICINE PACKAGING DEVICE

(75) Inventors: Hiroyuki Yuyama, Toyonaka (JP); Fuminori Kondo, Toyonaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 0 days.

(21) Appl. No.: 12/962,539

(22) Filed: Dec. 7, 2010

(65) Prior Publication Data

US 2011/0139293 A1   Jun. 16, 2011

Related U.S. Application Data

(63) Continuation of application No. 12/594,788, filed as application No. PCT/JP2008/067173 on Sep. 24, 2008, now Pat. No. 7,861,495.

(30) Foreign Application Priority Data

Sep. 27, 2007 (JP) .................................. 2007-251621
Sep. 17, 2008 (JP) .................................. 2008-238308

(51) Int. Cl.
*B65B 1/30* (2006.01)
(52) U.S. Cl. .................. 53/396; 53/473; 53/246; 53/390
(58) Field of Classification Search ............... 53/396, 53/473, 474, 158, 539, 246, 390
See application file for complete search history.

(56) References Cited

U.S. PATENT DOCUMENTS

| | | | |
|---|---|---|---|
| 5,408,443 A | | 4/1995 | Weinberger |
| 7,177,721 B2* | | 2/2007 | Kirsch et al. ............ 700/236 |
| 7,203,571 B2* | | 4/2007 | Kirsch et al. ............ 700/236 |
| 7,861,495 B2* | | 1/2011 | Yuyama et al. ............ 53/246 |
| 2003/0074868 A1 | | 4/2003 | Yasuoka et al. |
| 2004/0134043 A1 | | 7/2004 | Uema et al. |
| 2005/0125097 A1 | | 6/2005 | Chudy et al. |
| 2006/0058917 A1 | | 3/2006 | Vonk et al. |
| 2006/0125356 A1 | | 6/2006 | Meek, Jr. et al. |

(Continued)

FOREIGN PATENT DOCUMENTS

JP        6-9602        2/1994

(Continued)

OTHER PUBLICATIONS

International Search Report for PCT/JP2008/067173, mailed Nov. 4, 2008 (3 pages).

(Continued)

*Primary Examiner* — Stephen F Gerrity

(74) *Attorney, Agent, or Firm* — Jones Day; Christopher C. Bolten

(57) ABSTRACT

There is provided a distributed medicine supplying device, which allows medicines to be distributed at a time relative to a plurality of prescription data and to be distributed appropriately in response to various types of requests. The distributed medicine supplying device includes: a receiving unit 7 for receiving prescription data; a storing unit 8 for storing an assignment condition to medicine to be accommodated in measures 4 of a tray 5; a central processing unit 10 for determining a position of the medicine to be distributed to each of the measures 4 of the tray 5 in accordance with the assignment condition stored in the storing unit 8 based on the prescription data 12 sequentially received by the receiving unit 7; and a displaying unit 9 for displaying the distribution position determined by the central processing unit 10.

8 Claims, 18 Drawing Sheets

U.S. PATENT DOCUMENTS

| | | | |
|---|---|---|---|
| 2006/0129272 A1* | 6/2006 | Kirsch et al. | 700/231 |
| 2008/0149657 A1* | 6/2008 | Kim | 221/2 |
| 2009/0152291 A1 | 6/2009 | Ohmura et al. | |
| 2009/0210247 A1* | 8/2009 | Chudy et al. | 705/2 |

FOREIGN PATENT DOCUMENTS

| | | |
|---|---|---|
| JP | 6-9603 | 2/1994 |
| JP | 6-37202 | 5/1994 |
| JP | 6-227523 | 8/1994 |
| JP | 7-108682 | 11/1995 |
| JP | 2509822 | 6/1996 |
| JP | 2866543 | 3/1999 |
| JP | 2001-212211 | 8/2001 |
| JP | 2004-203433 | 7/2004 |
| JP | 3650776 | 5/2005 |
| JP | 2006-151399 | 6/2006 |
| JP | 2007209600 A * | 8/2007 |
| JP | 2007297066 A * | 11/2007 |
| KR | 2003-0027785 | 4/2003 |
| TW | 200604893 | 2/2006 |
| WO | WO 99/60982 A2 | 12/1999 |
| WO | WO 02/38101 A2 | 5/2002 |
| WO | WO 2004/015505 A2 | 2/2004 |
| WO | WO 2005/111955 A1 | 11/2005 |
| WO | WO 2007/091375 A1 | 8/2007 |

OTHER PUBLICATIONS

Written Opinion for PCT/JP2008/067173, mailed Nov. 4, 2008 (4 pages).

European Search Report for Application No. 08832869.5-1238, mailed Mar. 4, 2011, 7 pages.

* cited by examiner

```
WARD
BUILDING : EAST WARD        2008/02/13
NAME        BUILDING
PATIENT ID : 10524281
PATIENT NAME: YUYAMA, ICHIRO
WARD : 4624
ENTRY No.    1 - 0 0 1
MEDICINE /  DTA No.    PRESCRIBED
   NAME                    DOSE
========================================
ADSORBIN (100mg)              1 TABLET
                             (2 TABLETS)
1,2,3,5,6,7,9,10,11
ASCORBIC ACID POWDER(200mg)  1 TABLET
                             (9 TABLETS)
4,8
                  -END-
```

(b)

```
WARD
BUILDING : EAST WARD        2008/02/13
NAME        BUILDING
PATIENT ID : 10524281
PATIENT NAME: YUYAMA, ICHIRO
WARD : 4624
ENTRY No.    1 - 0 0 1
MEDICINE /  DTA No.    PRESCRIBED
   NAME                    DOSE
========================================
ADSORBIN (100mg)              1 TABLET
                             (2 TABLETS)
4,8
ASCORBIC ACID POWDER(200mg)  1 TABLET
                             (9 TABLETS)
1~3, 5~7, 9~11
                  -END-
```

(c)

```
WARD
BUILDING : EAST WARD        2008/02/13
NAME        BUILDING
PATIENT ID : 10524281
PATIENT NAME: YUYAMA, ICHIRO
WARD : 4624
ENTRY No.    1 - 0 0 1
MEDICINE /  DTA No.    PRESCRIBED
   NAME                    DOSE
========================================
ADSORBIN (100mg)              1 TABLET
                             (2 TABLETS)
  .  .  .  .  4  .  .
  .  .  8  .  .  .  .
ASCORBIC ACID POWDER(200mg)  1 TABLET
                             (9 TABLETS)
  .  .  .  .  6  5  .
  .  .  .  .  11 10 .
  .  .  .  .  .  9  3
  .  .  .  .  .  .  2
  .  .  .  .  .  7  1
                  -END-
```

WARD    BED    PATIENT      PATIENT
                  ID          NAME 301      31   4124545712   YUYAMA,
                           TARO
301      32   5668911143   YUYAMA,
                           JIRO
301      33   1156879452   YUYAMA,
                           HANAKO

ENTRY No.   1-005

MEDICINE  / DTA No.    1 DOSE /
  NAME                TOTAL DOSE
==================================
ATARAX TABLET 25mg          1 TABLET
                          (3 TABLETS)
```

|   |   |   |   |   |   |   |   |   |    |   |
|---|---|---|---|---|---|---|---|---|----|---|
| • | • | • | • | • | • | • | • | • | 12 | • |
| • | • | • | • | • | • | • | • | • | 11 | • |
| • | • | • | • | • | • | • | • | • | 10 | • |
| • | • | • | • | • | • | • | • | • | •  | • |
| • | • | • | • | • | • | • | • | • | •  | • |
| • | • | • | • | • | • | • | • | • | •  | • |

ALINAMIN TABLET          2 TABLET
                       (12 TABLETS)

|   |   |   |   |   |   |   |   |    |   |   |
|---|---|---|---|---|---|---|---|----|---|---|
| • | • | • | • | • | • | • | • | •  | • | • |
| • | • | • | • | • | • | • | • | •  | • | • |
| • | • | • | • | • | • | • | • | •  | • | • |
| • | • | • | • | • | • | • | • | 15 | 9 | • |
| • | • | • | • | • | • | • | • | 14 | 8 | • |
| • | • | • | • | • | • | • | • | 13 | 7 | • |

WARFARIN TABLET 5mg       1 TABLET
                        (9 TABLETS)

|   |   |   |   |   |   |   |    |   |   |
|---|---|---|---|---|---|---|----|---|---|
| • | • | • | • | • | • | • | 18 | • | 6 |
| • | • | • | • | • | • | • | 17 | • | 5 |
| • | • | • | • | • | • | • | 16 | • | 4 |
| • | • | • | • | • | • | • | •  | • | 3 |
| • | • | • | • | • | • | • | •  | • | 2 |
| • | • | • | • | • | • | • | •  | • | 1 |

-END-

```
WARD     : EAST WARD        2008/08/01
BUILDING : BUILDING              19:48

WARD : 301
BED  : 32
PATIENT ID : 5668911143
PATIENT NAME: YUYAMA, JIRO

ENTRY No.   1 - 0 0 5

MEDICINE /  DTA No.    1 DOSE /
NAME                  TOTAL DOSE
========================================

ALINAMIN TABLET              2 TABLET
                           (6 TABLETS)
```

| . | . | . | . | . | . | . | . | . | . | . | . |
|---|---|---|---|---|---|---|---|---|---|---|---|
| . | . | . | . | . | . | . | . | . | . | . | . |
| . | . | . | . | . | . | . | . | . | . | . | . |
| . | . | . | . | . | . | . | . | . | 15 | . | . |
| . | . | . | . | . | . | . | . | . | 14 | . | . |
| . | . | . | . | . | . | . | . | . | 13 | . | . |

```
ATARAX TABLET 25mg           1 TABLET
                           (3 TABLETS)
```

| . | . | . | . | . | . | . | . | . | 12 | . |
| . | . | . | . | . | . | . | . | . | 11 | . |
| . | . | . | . | . | . | . | . | . | 10 | . |
| . | . | . | . | . | . | . | . | . | . | . |
| . | . | . | . | . | . | . | . | . | . | . |
| . | . | . | . | . | . | . | . | . | . | . |

-END- (b)

```
WARD     : EAST WARD        2008/08/01
BUILDING : BUILDING              19:50

WARD : 301
BED  : 33
PATIENT ID : 1156879452
PATIENT NAME: YUYAMA, HANAKO

ENTRY No.   1 - 0 0 5

MEDICINE /  DTA No.    1 DOSE /
NAME                  TOTAL DOSE
========================================

WARFARIN TABLET 5mg          1 TABLET
                           (3 TABLETS)
```

| . | . | . | . | . | . | . | . | 18 | . | . |
| . | . | . | . | . | . | . | . | 17 | . | . |
| . | . | . | . | . | . | . | . | 16 | . | . |
| . | . | . | . | . | . | . | . | . | . | . |
| . | . | . | . | . | . | . | . | . | . | . |
| . | . | . | . | . | . | . | . | . | . | . |

-END-

DISTRIBUTED MEDICINE SUPPLYING DEVICE AND MEDICINE PACKAGING DEVICE

CROSS-REFERENCE TO RELATED APPLICATIONS

This application is a continuation of U.S. patent application Ser. No. 12/594,788, filed Oct. 5, 2009, now U.S. Pat. No. 7,861,495, which is a national stage filing under 35 U.S.C. §371 of International Patent Application No. PCT/JP2008/067173, filed Sep. 24, 2008, which claims the benefit of Japanese Patent Application No. 2007-251621, filed Sep. 27, 2007, and also claims the benefit of Japanese Patent Application No. 2008-238308, filed Sep. 17, 2008, the entire contents of all of which are incorporated by reference herein.

TECHNICAL FIELD

The present invention relates to a distributed medicine supplying device, a medicine distributing method and a medicine packaging device.

BACKGROUND ART

There exists in the art a medicine packaging device including a distributed medicine supplying device, wherein a medicine that cannot be supplied in an automated manner (e.g., tablets) is manually prepared as separate packages and is then supplied to a packaging device. Such a distributed medicine supplying device is constructed to accommodate distributed medicines in a tray, which are compartmentalized in a latticed form, and supply the distributed medicines.

In the above-described conventional distributed medicine supplying device, medicines for one prescription are distributed through one tray, while medicines for the next prescription are distributed again after supplying the distributed medicines from said tray (see, e.g., Patent Documents 1 to 4)

Patent Document 1: Japanese Patent Application Laid-Open No. (Hei)6-37202

Patent Document 2: Japanese Patent No. 2866543

Patent Document 3: Japanese Patent Application Laid-Open No. 2004-203433

Patent Document 4: Japanese Patent Application Laid-Open No. 2006-151399

SUMMARY OF THE INVENTION

However, in the above-described conventional distributed medicine supplying device, medicines must be distributed again to the tray per prescription. This increases the number of performing such a process, thereby complicating the same. Further, hospitals generally have different requests regarding the distribution process. It is essentially impossible to accommodate all of such requests.

Thus, it is an object of the present invention to provide a distributed medicine supplying device, which allows medicines to be distributed at a time relative to a plurality of prescription data and to be distributed appropriately in response to various types of requests. The present invention also seeks to provide a medicine distributing method and a medicine packaging device.

A distributed medicine supplying device of the present invention, which is provided to solve the foregoing problems, is constructed to sequentially supply medicines accommodated in a plurality of measures defined in a tray. The distributed medicine supplying device comprises the following: a receiving means for receiving a prescription data; a storing means for storing an assignment condition for a medicine accommodated in each of the measures of the tray; a position determining means for determining a position of the medicine to be distributed to each of the measures of the tray in accordance with the assignment condition stored in the storing means based on the prescription data sequentially received by the receiving means; and a displaying means for displaying a distribution position determined by the position determining means.

According to such construction, it can be shown that the sequentially received prescription data are assigned in which position of each of the measures of the tray in accordance with the preset assignment condition. That is, medicines can be distributed to one tray based on a plurality of the prescription data, and the distribution position can be automatically determined in accordance with the preset assignment condition. Further, the position of the measures, for which the distribution process may be performed, can be displayed on the displaying unit.

Preferably, the assignment condition stored in the storing means includes an assignment by a maximum package number having a condition of not exceeding a maximum package number, which can be assigned to the tray. Further, the position determining means is preferably configured to at least sequentially count a package number of each of the prescription data received by the receiving means and to put an accumulated value of the counted package number as a maximum value not exceeding the maximum package number based on the assignment by a maximum package number stored in the storing means. This is to determine the position of the medicine to be distributed to each of the measures of the tray.

Preferably, the assignment condition stored in the storing means further includes at least one of the following conditions: an assignment per ward building; an assignment by a prescription number; an assignment by reception time; and a forced assignment. Further, the position determining means is preferably configured to determine the prescription data to be distributed to the tray when one of two or more of the assignment conditions including the assignment by a maximum package number is satisfied.

Preferably, the distributed medicine supplying device further comprises a distribution pattern selecting means for selecting a distribution pattern for the medicine accommodated in each of the measures of the tray.

The distribution pattern preferably includes at least one of the following sets: a continuation set for continually distributing the medicine in the order of the medicine supplied from each of the measures; and a measure-skipping set for skipping at least one measure to proceed to next distribution when a prescription changes.

Further, a medicine packaging device of the present invention, which is provided to solve the foregoing problems, is constructed to sequentially supply and package medicines accommodated in a plurality of measures defined in a tray. The medicine packaging device comprises the following: a receiving means for receiving a prescription data; a storing means for storing an assignment condition for a medicine to be accommodated in each of the measures of the tray; a position determining means for determining a position of the medicine to be distributed to each of the measures of the tray in accordance with the assignment condition stored in the storing means based on the prescription data sequentially received by the receiving means; and a displaying means for displaying a distribution position determined by the position determining means.

Preferably, the medicine packaging device further comprises: an extracting means for extracting a data relating to a distributed medicine, the data being included in the prescription data received by the receiving means; and a printing means for printing a distribution instruction showing that the medicine is distributed to which measures of the tray based on the data relating to a distributed medicine extracted by the extracting means.

According to such construction, before all the data relating to a distributed medicine assigned to the tray are prepared, the medicine may be distributed to the corresponding measures of the tray based on the printed descriptions of the distribution instruction. Thus, a package process may begin in relation to the medicine distributed in advance. Accordingly, work efficiency can be enhanced.

Preferably, the displaying means is configured to display an indication showing that a distribution process can start when the data relating to a distributed medicine is extracted by the extracting means.

According to such construction, an operator may begin the distribution process after checking the items displayed on the displaying unit. Thus, the distribution process may be performed at an appropriate time.

According to the present invention, since the distribution position on one tray can be determined relative to the sequentially-received prescription data in accordance with the assignment condition, the distribution process may be further simplified compared to the prior art. In addition, the distribution position may be specified in response to various types of requests in accordance with the assignment condition.

BRIEF DESCRIPTION OF THE DRAWINGS

FIG. 13 illustrates an example of a DTA instruction printed by a journal printer provided to a distributed medicine supplying device according to another embodiment.

FIG. 17 illustrates another example of a DTA instruction printed per Entry No.

FIG. 18 illustrates still another example of a DTA instruction printed per patient.

DESCRIPTION OF REFERENCE NUMERALS

Figure 1:
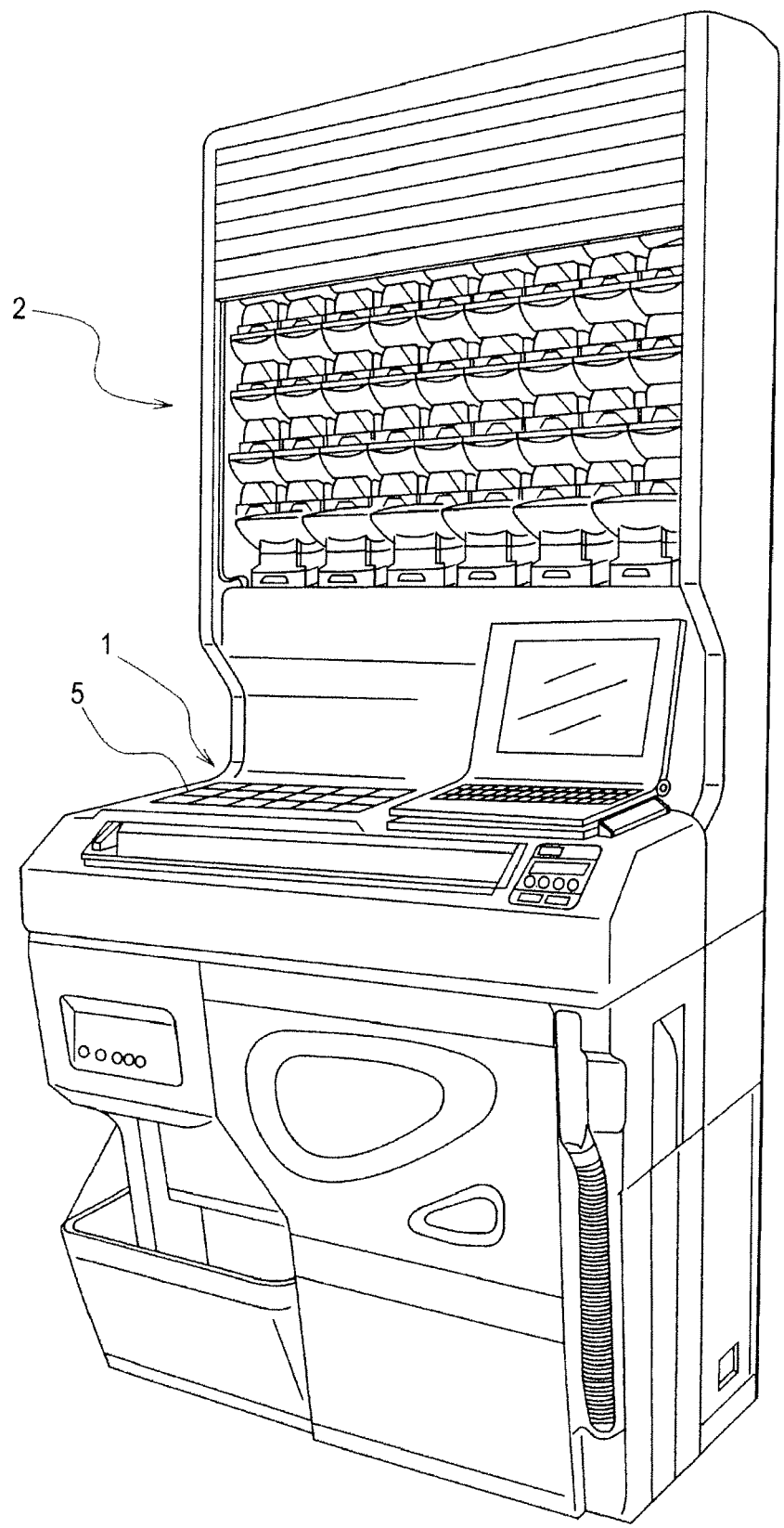
FIG. 1 is a perspective view of a medicine packaging device including a distributed medicine supplying device according to one embodiment.
Figure 2:
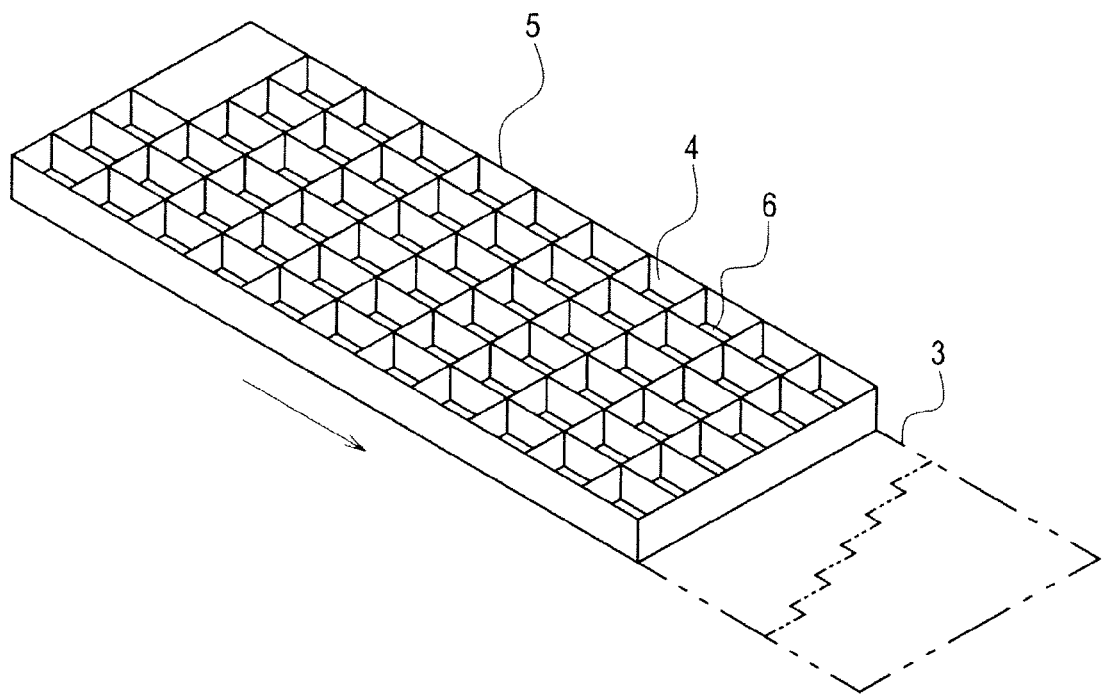
FIG. 2 schematically illustrates a tray employed in the distributed medicine supplying device of FIG. 1.
Figure 3:
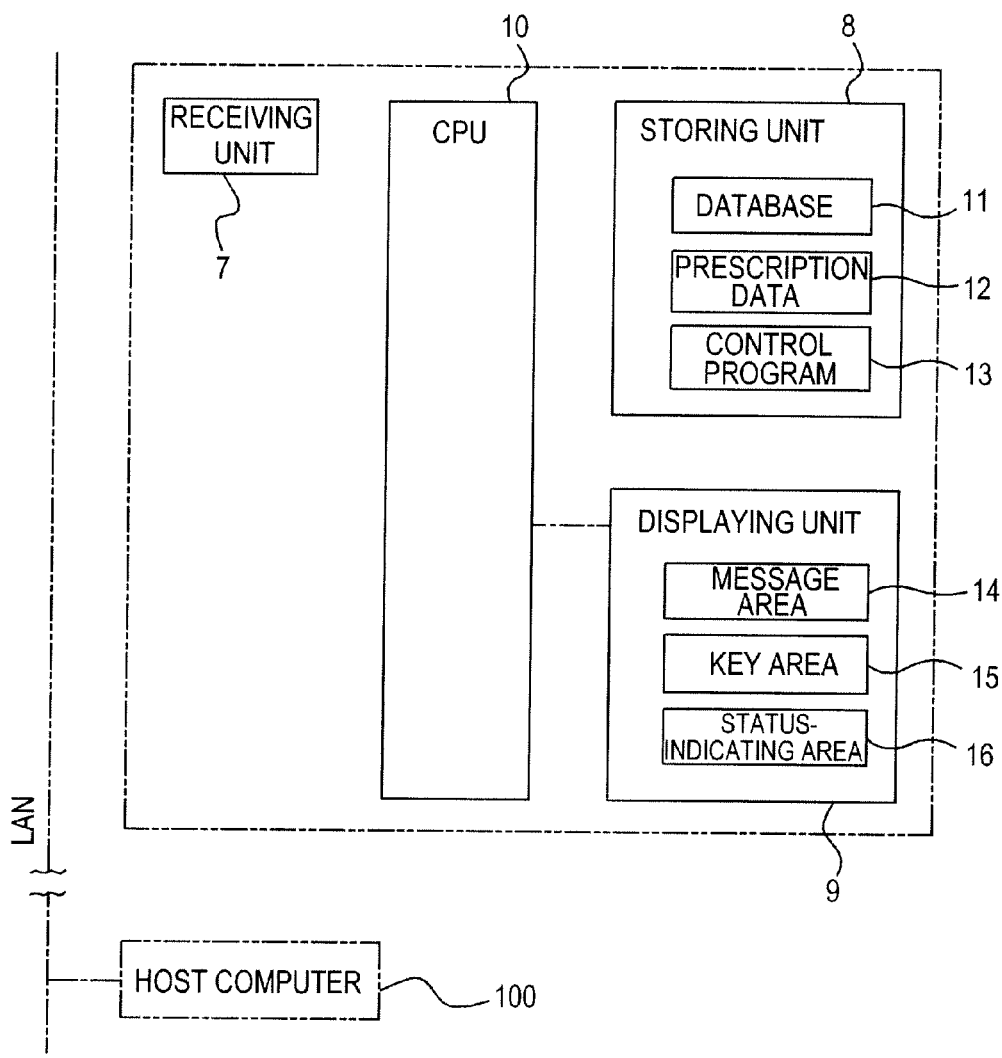
FIG. 3 is a block diagram of the distributed medicine supplying device of FIG. 1.
Figure 4:
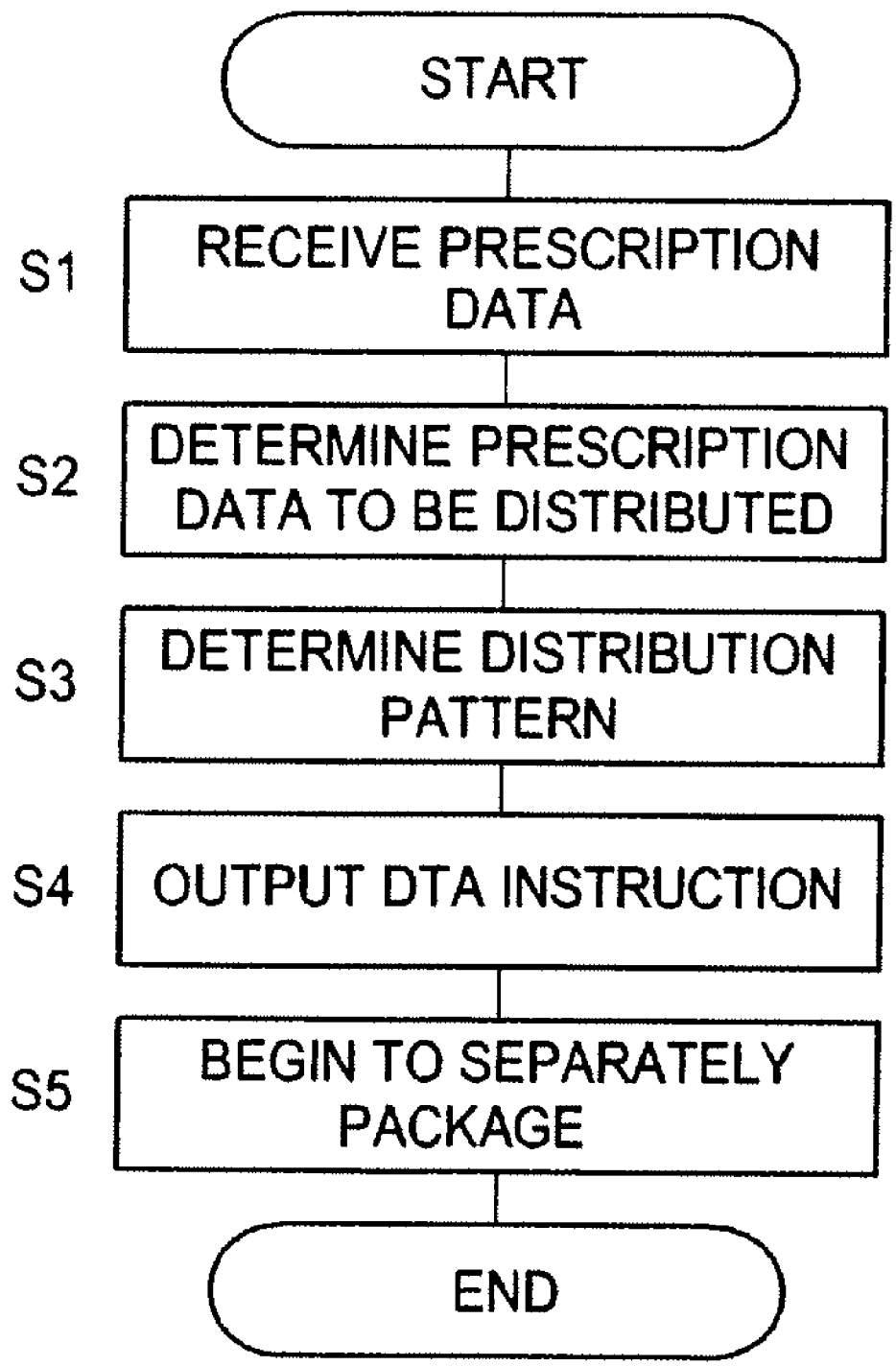
FIG. 4 is a flow chart showing processes performed at a central processing unit of the distributed medicine supplying device of FIG. 1.

1 . . . Distributed medicine supplying device
2 . . . Medicine packaging device
3 . . . Tray support
4 . . . Measure
5 . . . Tray
6 . . . Bottom plate
7 . . . Receiving unit
8 . . . Storing unit
9 . . . Displaying unit
10 . . . CPU
11 . . . Database
12 . . . Prescription data
13 . . . Control program
14 . . . Message area
15 . . . Button area
16 . . . Status-indicating area
17 . . . Function area
18 . . . Dedicated distribution device
19 . . . Screen
20 . . . Indicator
21 . . . Journal printer
22 . . . Barcode reader
23 . . . Display
100 . . . Host computer

DETAILED DESCRIPTION

Embodiments of the present invention will be described with reference to the accompanying drawings.

FIG. 1 illustrates a medicine packaging device 2 including a distributed medicine supplying device 1 according to one embodiment of the present invention. The distributed medicine supplying device 1 is used in order to set half tablets, special medicines, etc., which cannot be supplied in an automated manner, in a manual distribution manner (e.g., by means of a detachable tablet adapter (DTA)) for automatically packaging the same by a packaging paper.

The distributed medicine supplying device 1 is constructed as follows: a tray 5 defining a plurality of measures 4, which are arranged in a latticed form to accommodate distributed medicine, is placed on a tray support 3; the tray 5 is slidably moved horizontally by a tray conveying unit (not shown); and the distributed medicine in each of the measures 4 is supplied by sequentially opening bottom plates 6 of the respective measures 4. The tray 5 is configured to have sixty-three measures (i.e., 6-row×11-column, three measures are closed) so that a maximum package number is set at 63 (three measures are not utilized). Further, a base plate having an opening with a stepped inner edge is provided at a bottom side of the tray 5.

Thus, if the tray 5 is horizontally moved, then the bottom plates 6 are sequentially opened from one side toward the opposite side in each column.

The distributed medicine supplying device 1 includes a receiving unit 7, a storing unit 8, a display unit 9 and a central processing unit (CPU) 10. Preferably, these units are configured to use a computer (e.g., PC), which is separately provided for the medicine packaging device, rather than for the distributed medicine supplying device 1

The receiving unit 7 is configured to receive a prescription data 12 outputted from a host computer 100 via a Local Area Network (LAN).

The storing unit 8 is configured to store the received prescription data 12, a database 11 having various master files and a control program 13.

The display unit 9 may include a Liquid Crystal Display (LCD). If necessary, it may include a touch panel. In this embodiment, the display unit 9 comprises a touch panel. The touch panel includes a message area 14, a button area 15, a status-indicating area 16 and a function area 17.

Statuses of the medicine packaging device 2 or error messages are displayed in the message area 17. For example, in a status where a separate package process can be performed, a message "Waiting. A separate package process can be performed" may be displayed.

In the button area 15, manipulation buttons (e.g., at maximum, six manipulation buttons) are provided to implement operations that must be timely made according to each status of the medicine packaging device 2. For example, in case of the waiting status, buttons are displayed such as a "START" button, an "OPEN/CLOSE DTA" button, etc.

In the status-indicating area 16, there is displayed the contents of the prescription data 12, which relates to a medicine under separate package process, or the status of the medicine packaging device 2. Specifically, the following items may be displayed: a package number (the number of remaining packages of the prescription under current package process); a patient ID (a patient ID of the data under package process); a patient name (a patient name pertinent to the data under package process); an exchange coupon number (an exchange coupon number of the data under package process); a dose times per day; a dosing days number (a dose times per day and a dosing days number of the data under package process); continuation or repetition (packaging order of the data under package process); a specification of tablets (a specification of tablets of the data under package process); a paper-remaining amount (the remaining amount of papers for separate package is displayed with five steps); a DTA reservation number (the current reservation number of the DTA); temperature (temperature of a heater roller); and communication (a communication state between the medicine packaging device 2 and the PC).

Figure 5:
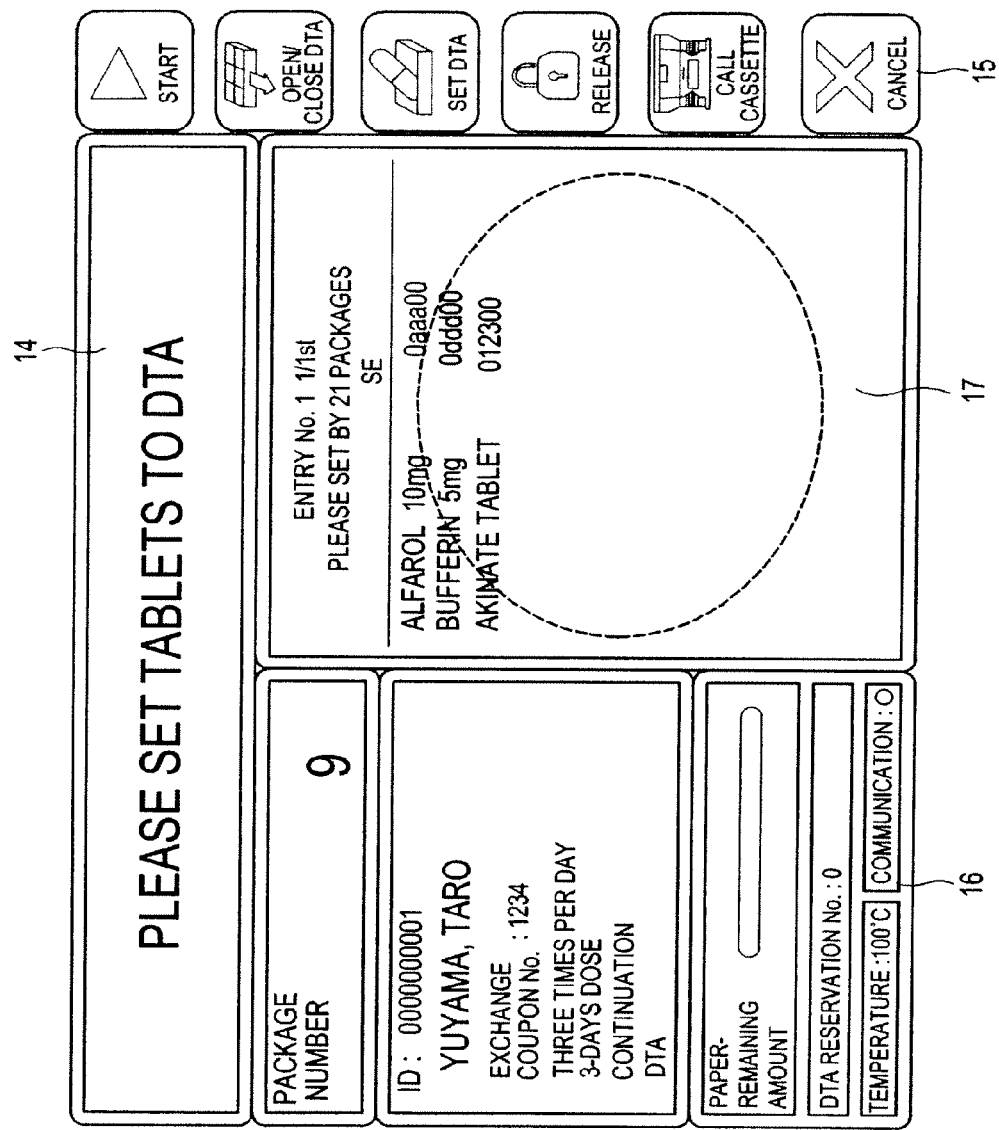
FIG. 5 illustrates a DTA-setting waiting screen displayed in a displaying unit of the distributed medicine supplying device of FIG. 1.
Figure 6:
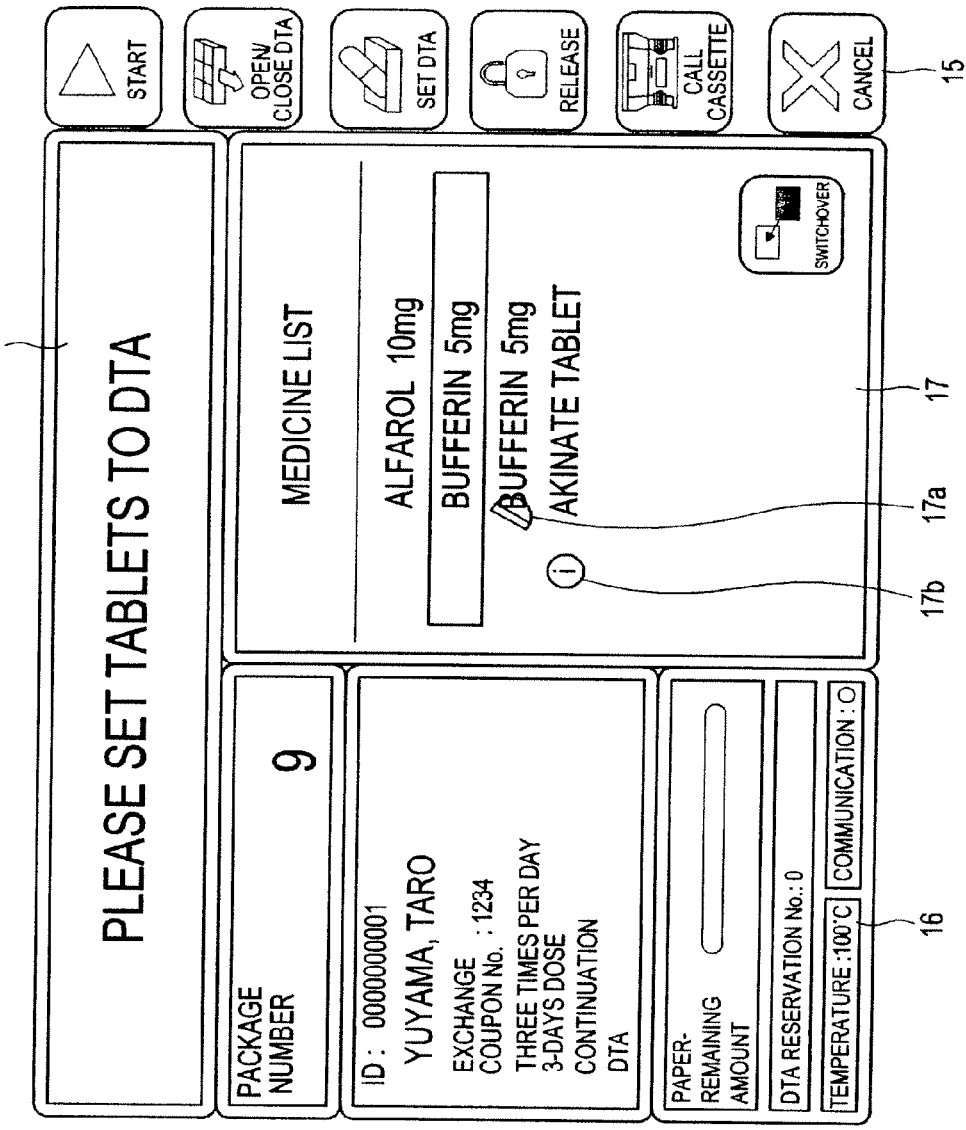
FIG. 6 illustrates a medicine-listed screen displayed by manipulating a detailed-distributing button.
Figure 7:
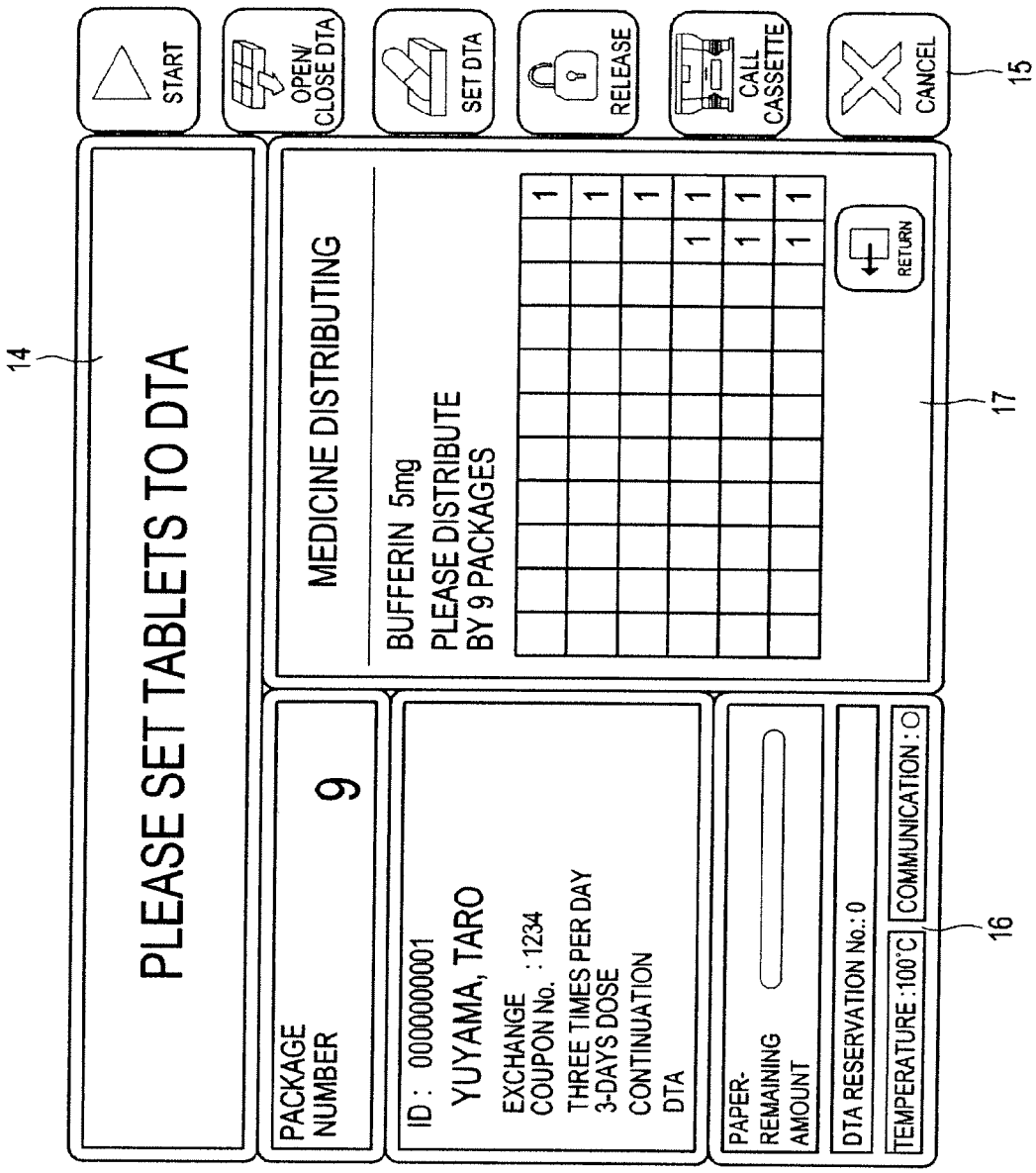
FIG. 7 illustrates a detailed-distributing screen displayed through a switchover by selecting any one of the medicine in FIG. 6.

In the function area 17, there are displayed the contents of a prescription or the indications relating to performing various operations. For example, as illustrated in FIG. 5, a setting-waiting screen is displayed. The setting-waiting screen includes items such as medicine names, a prescription amount, etc., which are included in the prescription data 12, other than detailed processed matters pertinent to the item displayed in the message area 14. When the function area 17 is manipulated through the setting-waiting screen, a medicine-listed screen illustrated in FIG. 6 is displayed. In the medicine-listed screen, a symbol 17a representing a half tablet is displayed beside some medicine that must be distributed in the form of a half tablet. As a result, it can be conveniently recognized which tablet must be distributed in the form of a half tablet. Further, in the medicine-listed screen, an "i" mark 17b is displayed with regard to some medicine to be distributed in a pattern different from a typical distribution pattern, thereby having users pay attention thereto. For example, in case of a biweekly-dosed medicine, an irregular distribution method is carried out, wherein such a medicine is not distributed sequentially along each of the measures 4 of the tray, but distributed along with any spacing. By having users pay attention to such a medicine, the users cannot make a mistake as to the distribution position. Furthermore, when the medicine name to be distributed is touch-manipulated in the medicine-listed screen, a detailed-distributing screen similar to a plane figure of the tray 5 is displayed as illustrated in FIG. 7. In the detailed-distributing screen, it is displayed by means of numerical characters (e.g., 1, 2, ½ (half), ¼ tablet, etc.) that the medicine touch-manipulated in the medicine-listed screen is distributed into which measures 4 and how much of the medicine is distributed.

The CPU 10 carries out the control program 13 by referring to the database 11 based on the prescription data 12 as described below.

Operations of the distributed medicine supplying device 1 will be described below.

First, the prescription data 12 relating to tablets to be distributed to the tray 5 are received in sequence (Step S1). Also, the prescription data 12 to be assigned to one tray 5 are determined (Step S2). Determining the prescription data 12 to be assigned is carried out based on the assignment conditions.

Such an assignment to one tray 5 is finished when one of the assignment conditions is satisfied. An assignment process then proceeds to the next tray 5. Specifically, the assignment conditions include: "assignment by a maximum package number"; "assignment per ward building"; "assignment by a prescription number"; "assignment by reception time"; and "forced assignment."

In "the assignment by a maximum package number," the package numbers included in the respective received prescription data 12 are counted in sequence. Also, the prescription data 12 are assigned to one tray 5 under the condition that an accumulation value of the counted package numbers becomes a maximum value that does not exceed the number of all the measures defined in the tray 5. The prescription data 12, wherein the accumulation value exceeds the maximum value of the measures 4, is set to be distributed at the next tray 5.

In "the assignment per ward building," an assignment process is based on whether data relating to a ward building, which are included in the sequentially-received prescription data 12, are the same or not. When it is determined that a ward building changes, the prescription data 12, which are received by that time, are collectively assigned to one tray 5.

In "the assignment by a prescription number," the received prescription data 12 are assigned to one tray 5 until the number thereof comes to a preset prescription number.

In "the assignment by reception time," in case a reception interval between the received prescription data 12 exceeds a preset appointment time, the prescription data 12 received by that time are assigned to one tray 5.

In "the forced assignment," assignment to one tray 5 is stopped by manipulating a closing button, even though an assignment process is being performed. The assignment process then proceeds to the next tray 5.

By way of example, the prescription data 12 may be received in the following order: a prescription A (including medicines to be manually distributed by twenty-one packages); a prescription B (including medicines to be manually distributed by twenty-one packages); a prescription C (including medicines to be manually distributed by seven packages); a prescription D (including medicines to be manually distributed by seven packages); and a prescription E (including medicines to be manually distributed by seven packages). In such a case, since the package number comes to sixty-three (i.e., maximum value) when receiving the prescription E, the manual distribution process on the prescriptions A to E may be performed for one tray. However, in case the prescriptions A to D are allocated to the ward building M and the prescription E is allocated to the ward building N, the manual distribution process on only the prescriptions A to D is performed for one tray and the manual distribution process on the prescription E is performed at the next tray 5, although assignment to one tray is not made by the maximum package. Further, in case the number of prescriptions for one tray is set as three, the manual distribution process on only the prescriptions A to C is performed, whereas the manual distribution process on the prescription D and other prescriptions subsequent therefrom are performed for the other tray 5. Also, in case an interval between the reception of the prescription B and the reception of the prescription C exceeds the preset time, the manual distribution process on only the prescriptions A and B is performed for one tray, whereas the manual distribution process on the prescription C and other prescriptions subsequent therefrom is performed for the other tray. In case the closing button is manipulated during the manual distribution process on the prescription A, only the manual distribution process on the prescription A is performed for one tray.

Further, it may not be necessary to set all of the five assignment conditions. User's arbitrarily choosing may be also possible. For example, in case of a hospital with only one ward building, the assignment per ward building is no longer necessary.

Next, if the prescription data 12 to be assigned to one tray 5 are determined under the condition that one of said assignment conditions is satisfied, then a distribution pattern for such a tray 5 is determined (Step S3).

The distribution pattern may include, for example, "a continuation set," "a measure-skipping set," "a column-changing set," etc. In such a case, preferably, as one of the distribution patterns is preset, a latticed frame corresponding to the measures 4 of the tray 5 may be displayed in the display unit 9 and each of the prescriptions may be distinguishably displayed according to the distribution pattern. By way of example, in case the prescription A includes three packages, "A1," "A2" and "A3" may be displayed in the frame in sequential package order. Thus, it can be confirmed at a glance which medicine must be manually distributed to which measures 4.

When a manual distribution process must be continuously performed relative to each of the measures 4 of the tray 5 from a measure first locating in opening order one after another, "the continuation set" is set. In "the continuation set," even if the prescription data 12 changes, the continuous distribution process can be performed without skipping the measures 4. As a result, it is possible to distribute the medicines to one tray 5 as much as possible.

In "the measure-skipping set," the distribution process is performed continuously in opening order along each of the measures 4 of the tray 5 relative to each of the prescription data 12. However, if the prescription data 12 changes, then at least one measure is skipped and the next distribution process continues. Thus, medicines can be distributed to one tray 5 as much as possible. Also, it is possible to prevent misdistribution from occurring between the prescription data.

In "the column-changing set," the distribution process is performed continuously in opening order along each of the measures 4 of the tray 5 relative to each of the prescription data 12 in the same manner as "the measure-skipping set." However, when the prescription data 12 changes, the distribution process is performed in the next column by changing a column. Thus, each of the prescription data can be clearly classified. Also, it is possible to further prevent the mistake of distribution compared to "the measure-skipping set."

With regard to the assignment conditions, the prescription data 12 for one tray is determined on the assumption that the distribution pattern is set as "the continuous pattern." Thus, if "the measure-skipping set" or "the column-changing set" is established, then it becomes necessary to correct processes on the prescription data 12 to be assigned to one tray such that the assignment conditions can be satisfied under such distribution pattern. For example, when "the measure-skipping set" is set with regard to said prescriptions A to E, the prescription E cannot be assigned. In such a case, it is required that the distribution process on the prescription E is performed in the next tray 5.

If the prescription data 12 to be assigned to each tray 5 and the distribution pattern are determined in such a manner as described above, then an instruction for the manually-distributed medicines (manual-distribution instruction, DTA instruction, etc.) is outputted (Step S4).

That is, a DTA-setting waiting screen illustrated in FIG. 5 is displayed in the display unit 9. Since names of medicines to be distributed are displayed in the DTA-setting waiting screen, a user may manually distribute the corresponding medicines to the tray 5. Alphabetical characters and numerical characters, which are displayed adjacent to the medicine name on the right side thereof, indicate when and how much to take the medicine in connection with dose times per day (e.g., six times). Accordingly, the distribution process may be performed according to such alphabetical or numerical characters. Further, by directly manipulating the DTA-setting waiting screen, the medicine-listed screen as illustrated in FIG. 6 may be displayed. In this medicine-listed screen, the symbol 17a that represents a half tablet is displayed beside the medicine name of a half tablet, thereby providing at-a-glance discrimination and preventing the distribution mistake. In such a case, a distinguishable symbol such as *, ⨯, etc. may be displayed for any medicine relating to a prescription with special contents (e.g., a prescription including dose every other day, a prescription including different dose times at dosing time such as three times at morning, two times at afternoon, one time at evening, etc.) (In an example illustrated in FIG. 6, the "i" mark 17b is displayed).

Further, as to distributing which medicine to which measures 4, the medicine name displayed in the medicine-listed screen may be selected. Frame lines, which correspond to the respective measures 4 of the tray 5, and the name of the medicine to be distributed are displayed in the detailed-distributing screen. The amount of the medicine that is distributed in distribution order in accordance with the assignment conditions and the distribution pattern that are determined in the above-described manner are displayed as numerical characters within the frame line. Thus, a user may perform the distribution process with reference to such displayed indication. Accordingly, an efficient and exact manual distribution process may be performed. Moreover, even an unskilled pharmacist can accurately cope with the distribution process. In particular, a medicine having an irregular dose time may be effectively managed.

After the distribution process for the selected medicine is completed, when a "RETURN" button displayed in the detailed-distributing screen is manipulated, the medicine-listed screen as shown in FIG. 6 is displayed again. Then, a character such as "COMPLETED" is displayed on the left side of the medicine that has been distributed completely. A user may select the medicine name in sequence and may allow above-described procedures to be repeated until the characters "COMPLETED" are displayed for all the medicine names.

After the distribution process for one tray is completed, the distributed medicines are automatically dispensed out of each of the measure 4. They are then packaged by one package at a time by a packaging device according to the prescription data 12.

The present invention should not be limited to the above-described embodiment. It should be appreciated that various modifications may be made within the subject matter of the appended claims.

In the foregoing embodiment, an image corresponding to the measures 4 of the tray 5 is displayed in a screen. However, medicines to be distributed and corresponding measures 4 may be notified via a voice (e.g., a voice "Please distribute a tablet A to each of the first to third measures one by one" may be emitted).

In the foregoing embodiment, assigning the prescription data 12 to each tray 5 is first determined. Then, the distribution pattern is determined. However, these processes may be performed in a reverse order. That is, if assigning the prescription data 12 to each tray 5 is determined after determination of the distribution pattern, then the above-described correction process becomes unnecessary.

Figure 8:
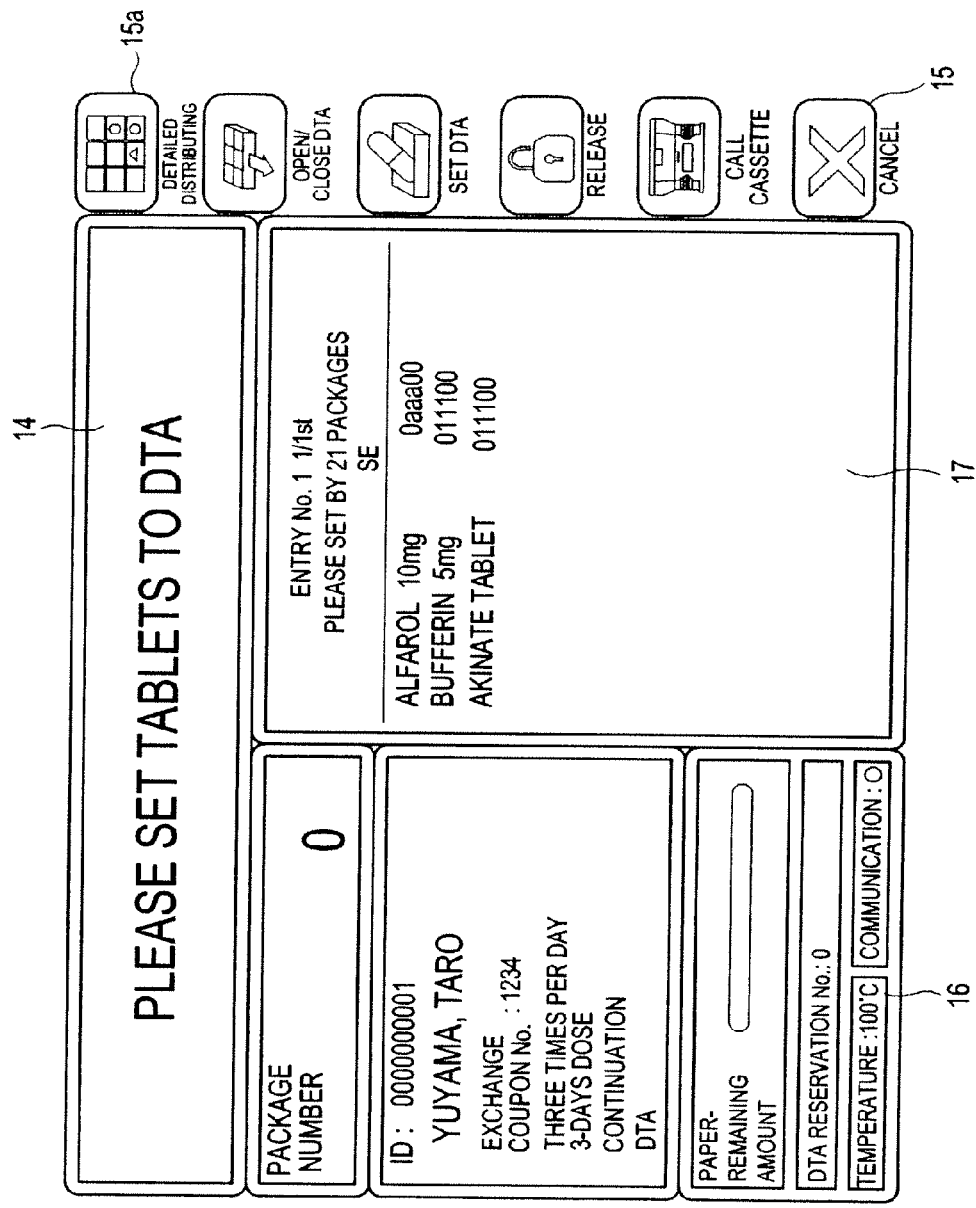
FIG. 8 illustrates another example of the DTA-setting waiting screen displayed on the displaying unit of the distributed medicine supplying device of FIG. 1.
Figure 9:
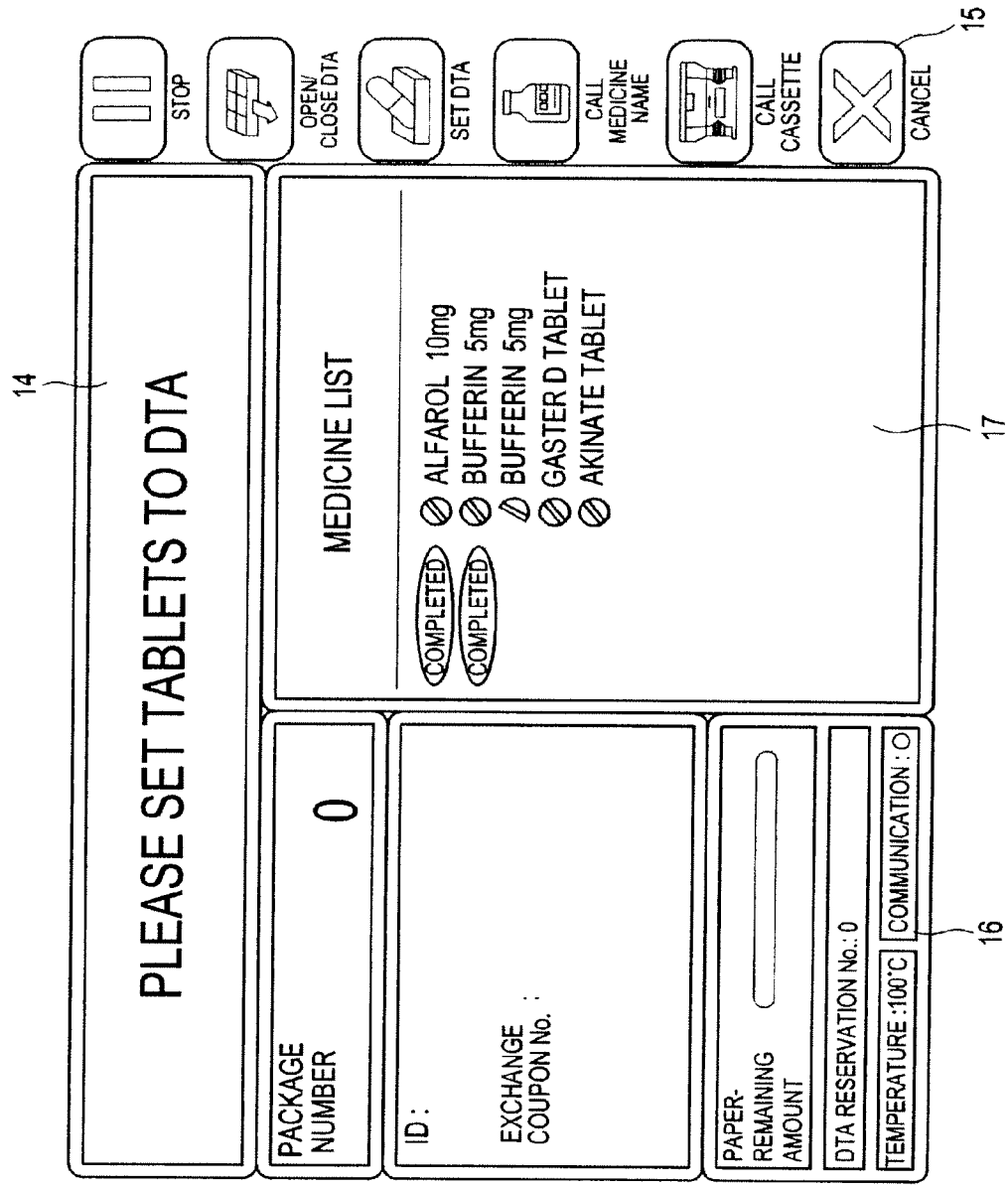
FIG. 9 illustrates a medicine-listed screen displayed by manipulating a detailed-distributing button in FIG. 8.
Figure 10:
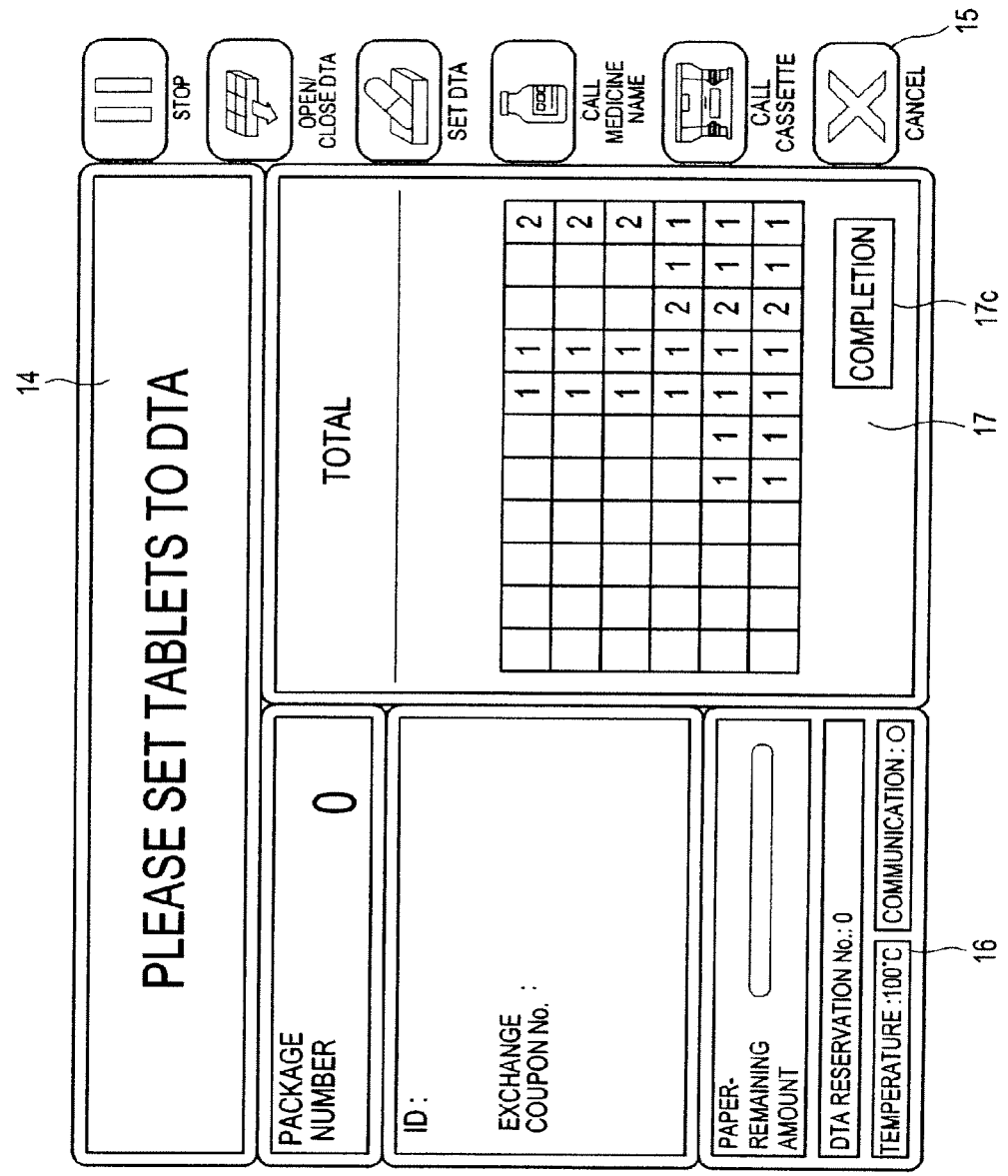
FIG. 10 illustrates a detailed-distributing screen displayed through a switchover by selecting any one of the medicine in FIG. 9.

In the foregoing embodiment, switchover to the medicine-listed screen is performed by directly manipulating the DTA-setting waiting screen. However, as illustrated in FIG. 8, a detailed-distributing button 15*a* may be provided and the switchover may be performed by manipulating the button 15*a*. Further, in the medicine-listed screen, a symbol representing a whole tablet may be displayed in addition to the symbol representing a half tablet. Furthermore, in the detailed-distributing screen shown in FIG. 10, if the distribution process on any medicine is completed and then a completion button 17*c* is manipulated, then the medicine-listed screen shown in FIG. 9 may be displayed again and a mark of "COMPLETED" may be displayed adjacent to such completed medicine at the left side thereof.

In the foregoing embodiment, specifying distribution position on the tray 5 is performed only through the display of the displaying unit 9. However, specifying distribution area on the measures 4 may be performed using LEDs provided to each of the measures 4 of the tray 5. In such a case, preferably, several LEDs with different colors respectively may be provided and the respective colors of the LEDs may match to colors (different per kinds of medicines) shown together with the medicine names in the screen, thereby making sure that which medicines correspond to which measures. This allows a user to easily know to distribute the medicines to which measure by the colors shown together with the medicine name in the screen and the colors of the LEDs turned on in conjunction with to the measures of the tray, thereby providing an efficient distribution process.

Figure 11:
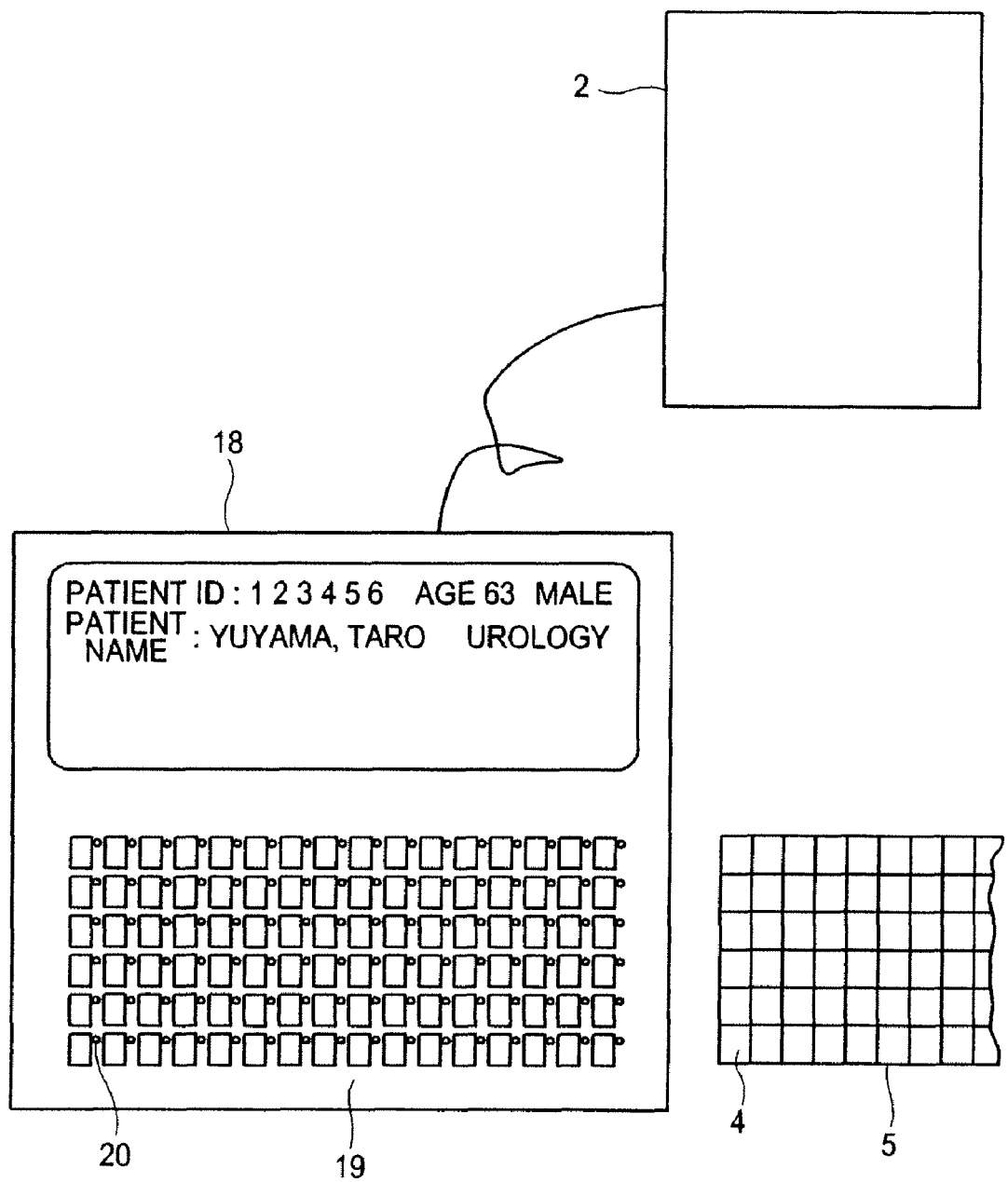
FIG. 11 schematically illustrates a dedicated distribution device employed in a medicine packaging device according to another embodiment.

Further, instead of providing LEDs to each of the measures 4 of the tray 5, a dedicated distribution device 18 that is configured to be capable of wired communication (or wireless communication) as illustrated in FIG. 11 may be provided. In such a case, a display screen of the dedicated distribution device 18 displays not only the same matters as those displayed in the above-described screen but also a lattice-formed image 19 corresponding to the measures 4 of the tray 5. Also, indicators 20, which are different in color from one another according to the types of medicines, are displayed as corresponding to respective sections of the displayed image 19 that are compartmentalized in a latticed form. Thus, as described above, it can be shown at a glance that medicines must be accommodated in which measures 4. As the dedicated distribution device 18 may be disposed in the immediate vicinity of the tray 5, correspondence relationship between each of the measures 4 of the tray 5 and the image 19 displayed in the screen may be more accurately understood. Preferably, the dedicated distribution device 18 may define apertures arranged in a latticed form corresponding to the measures 4 of the tray 5 and the dedicated distribution device may be configured such that when the tray 5 is set, the respective measures 4 are correspondingly positioned against the respective apertures. According to such an arrangement, setting a conventional tray 5 to the dedicated distribution device 18 allows the measures 4 that must accommodate medicines to be immediately distinguished, thereby greatly enhancing workability and preventing mistake on accommodation.

In the foregoing embodiment, it is confirmed in a visual manner whether or not medicines are properly accommodated to each of the measures 4 of the tray 5. However, the medicine accommodated in each of the measures 4 may be verified by photographing the entire tray 5 from its upper side with a camera, etc. In such a case, preferably, it may be judged whether each of the measures 4 accommodates the appropriate amount of medicine and such judgment result may be displayed on the displaying unit 9. Further, preferably, in case medicines are accommodated in an unintended place, an alarm may be emitted by a buzzer, etc. Furthermore, an openable and closable shutter may be provided to each of the measures 4. Also, only the shutters of the measures that must accommodate a medicine may be opened, while other shutters of the measures may be closed. In case of providing the shutters, it is possible to accurately accommodate a medicine to predetermined measures 4 without mistaking the measures 4 that must accommodate the medicine.

Further, in the foregoing embodiment, the distribution pattern is displayed on the screen. However, a DTA instruction may be printed by a journal printer in a timely manner when the distribution prescription is detected.

Figure 12:
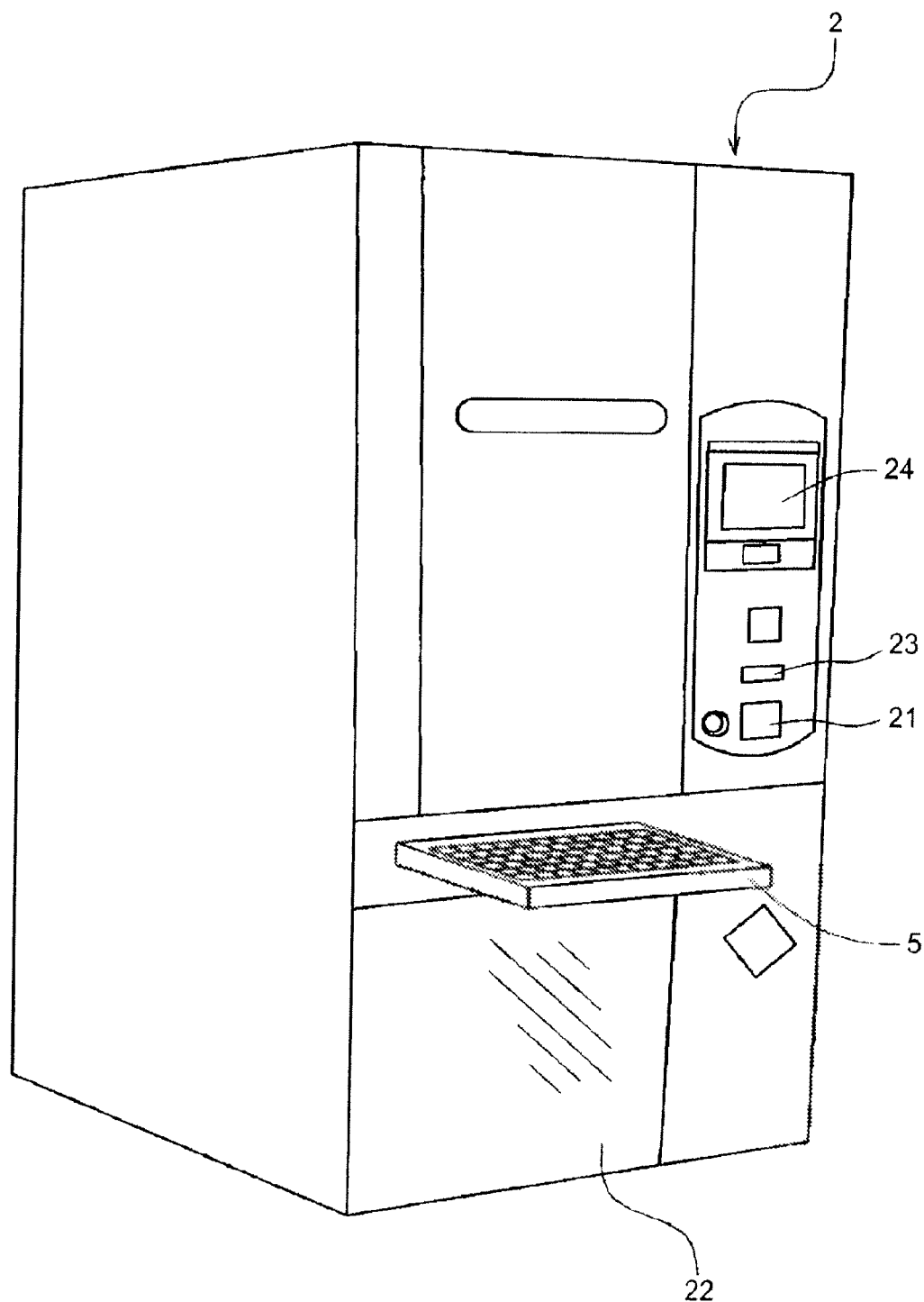
FIG. 12 is a perspective view schematically illustrating a medicine packaging device according to yet another embodiment.

In such a case, the medicine packaging device 2 may be configured to include a journal printer 21, as illustrated in FIG. 12. In the medicine packaging device 2, the tray 5 of the distributed medicine supplying device is provided so that it can be drawn out from a device body. The tray 5 is drawn out only when a medicine is distributed to each of the measures 4. Also, when a medicine is packaged, the tray is received in the device body 19. A packaging unit 22 is disposed below the tray 5. Further, a barcode reader 23 is disposed above the journal printer 21, thereby allowing barcodes on packaging boxes for vials or medicines to be read out and allowing a medicine to be specified with reference to a stored database. Further, a display 24 is disposed above the barcode reader 23.

Printed descriptions of the DTA instruction printed by the journal printer 21 include the following: a date; a ward building name; patient information (e.g., a patient ID, a patient name, a ward, etc.); and an Entry No. (e.g., the entry number of a tray); and prescription information, as illustrated in FIG. 13(*a*). The Entry No. consists of an identification number of the medicine supplying device (e.g., in case of only one device, merely "1") and an identification number of a tray for dispensing medicines. The prescription information of every medicine includes the following: a measure number of the tray 5 for manual distribution; a medicine name; a standard amount (e.g., weight per medicine); a DTA medicine amount per one dose (e.g., the amount of a manually-distributed medicine); a total DTA medicine amount; and a DTA measure number. It may further include, if necessary, a code number of a medicine maker, a HIS medicine code, etc. for every medicine.

Figure 14:
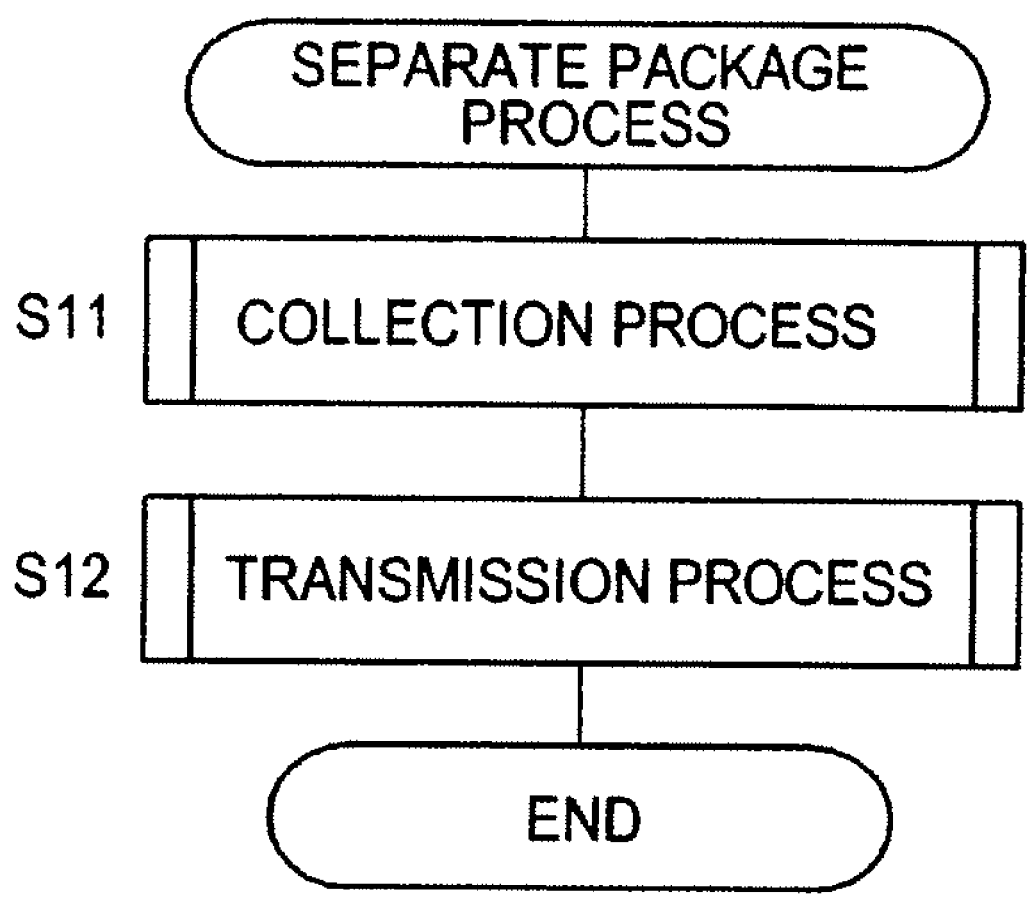
FIG. 14 is a flow chart showing a separate package process in the distributed medicine packaging device according to another embodiment.

When printing the DTA instruction, as shown in FIG. 14, a plurality of data are collected by means of a separately-provided computer (PC) receiving the data from the host computer 100 (Collection process: Step S11). Subsequently, the Entry No. is transmitted to the medicine packaging device 2 (Transmission process: Step S12).

Figure 15:
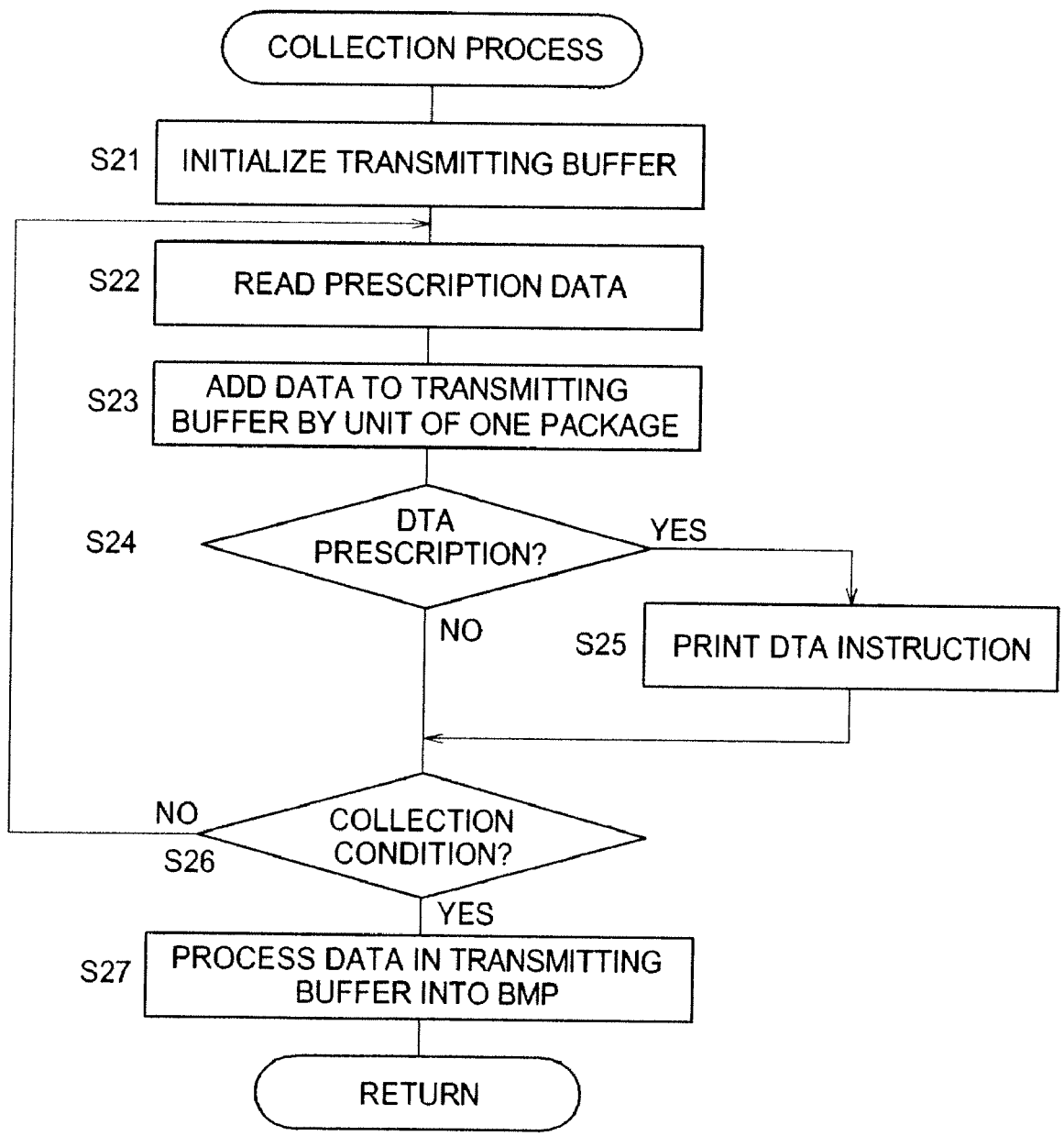
FIG. 15 is a flow chart showing a collection process of FIG. 14.

In the collection process, as shown in FIG. 15, a transmitting buffer is initialized (Step S21), the prescription data is read (Step S22) and the data is added to the transmitting buffer by unit of one package (Step S23). For example, if a prescription data includes a 3-day prescription containing a dose after "breakfast," "lunch" and "supper" per one day, then the data corresponding to nine packages are added. After the data is added to the transmitting buffer as described above, it is determined whether or not there is a prescription containing a DTA prescription, i.e., a prescription containing a medicine to be manually distributed (Step S24). If the DTA prescription is contained, then printing a DTA instruction begins by the journal printer (Step S25). If the DTA prescription is not contained, then it is determined whether or not a collection condition is satisfied instead of beginning to print the DTA instruction (Step S26). In such a case, the collection condition being satisfied means that one of the assignment conditions (which include "the assignment by a maximum package number," "the assignment per ward building," "the assignment by a prescription number," "the assignment by a reception time" and "the forced assignment", as described above) is satisfied. If the collection condition is not satisfied, then the process returns to Step S22 and the above-described processes are repeated. If the collection condition is satisfied, then the data in the transmitting buffer is processed into bit map (BMP), thereby preparing for printing a packaging paper in the medicine supplying device (Step S27).

Figure 16:
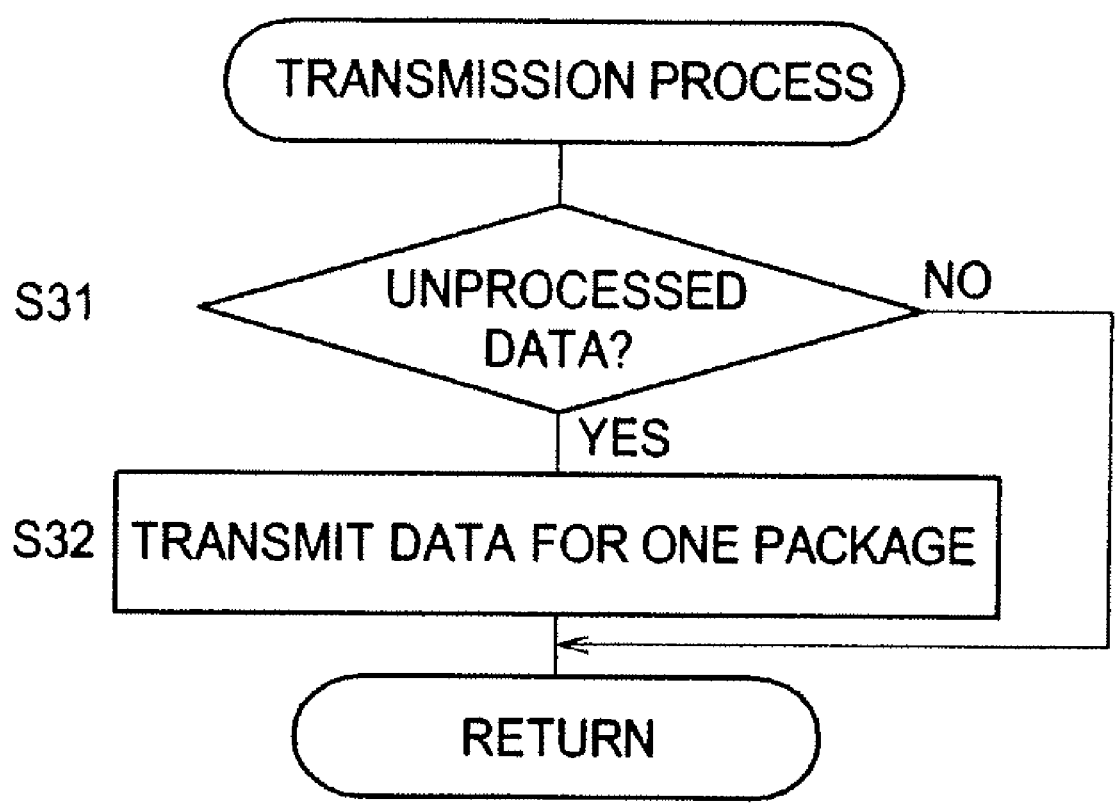
FIG. 16 is a flow chart showing a transmission process of FIG. 14.

In the transmission process, as shown in FIG. 16, it is determined whether unprocessed data remains in the separately-provided PC (Step S31). If the unprocessed data remains, then a data for one package is transmitted to the medicine packaging device 2 (Step S32). Thereafter, if the unprocessed data does not exist, then the transmission process is completed.

Since the DTA instruction is printed by the journal printer whenever the prescription data contains the DTA prescription as described above, an operator can begin the distribution process immediately upon taking a look at the printed descriptions. In such a case, preferably, an advance notice that the distribution process is possible may be displayed on the displaying unit 9 of the medicine packaging device 2 based on the transmitted Entry No. Such display may be made whenever the journal printer prints. Alternatively, it may be made after collecting the same Entry Nos. In case of displaying whenever the journal printer prints, an operator takes a look at such display and can then begin to perform the distribution process of distributing a medicine to each of the measures of the corresponding tray while checking the printed descriptions of the DTA instruction before completing the assignment process. Accordingly, although the sequentially-received prescription data containing a medicine to be manually distributed are small, it is advantageously possible to immediately begin the distribution process as soon as the data relating to the medicine to be distributed is inputted. Further, preferably, if all the medicines to be distributed are accommodated in the tray, then a display purporting that the manual distribution has been completed and a package process has started (e.g., Proper 1-001 DTA Setting) may be made at that point of time. As such, since it is notified when the package process must start, an operator can proceed with the process at his or her ease.

As for the DTA measure number printed on the DTA instruction, the data acquired by the above-described method of determining the distribution pattern may be used. Further, the printed descriptions on the DTA instruction may be changed, for example, in the following manner. In a DTA instruction illustrated in FIG. 13(b), when the DTA measure numbers are serial by three measures or more for each medicine, the DTA measure numbers are printed as intervening numbers are omitted using a symbol such as "~". In a DTA instruction illustrated in FIG. 13(c), the DTA measure numbers are printed for each medicine in a manner that shows that the medicine must be manually distributed to which sections of a latticed form corresponding to the respective measures 4 of the tray 5 and be distributed in what order. Thus, in case a plurality of medicines, it is possible to manually distribute only one of the medicines intensively and then proceed to the next medicine, thereby providing enhanced workability.

Further, when canceling the package process in the medicine supplying device, it is preferable that a prescription-cancelling confirmation may be displayed on a screen or printed. Thus, it can be confirmed via the screen and be left as a record by printing that a serious procedure such as cancellation is taken. Accordingly, an improper process can be prevented.

Further, in the foregoing embodiment, the DTA instruction is printed relative to the same patient and the same Entry No. However, it may be printed per an Entry No. or a prescription.

FIG. 17 illustrates an example of a DTA instruction that is printed per Entry No. The DTA instruction according to this example is printed with respect to medicines associated with the same Entry No. of 1-005, i.e., medicines that are manually distributed to the same tray of the same medicine supplying device. Thus, in case of medicines prescribed to several patients accommodated in the same ward, if the same Entry Nos. are provided thereto, then they can be collected and be manually distributed to the same tray.

FIG. 18 illustrates an example of a DTA instruction that is printed per patient. According thereto, the distribution process or the package process can start per patient.

The invention claimed is:

1. A distributed medicine supplying device for sequentially supplying medicines accommodated in a plurality of measures defined in a tray, comprising:

a receiving means for receiving a prescription data;

a storing means for storing an assignment condition for a medicine accommodated in each of the measures of the tray;

a barcode reader;

a medicine specifying means for reading a barcode on a packaging box for vials or medicines by means of the barcode reader and specifying a medicine with reference to the storing means;

a position determining means for determining a position of the medicine to be distributed to each of the measures of the tray in accordance with the assignment condition stored in the storing means based on the prescription data sequentially received by the receiving means; and a displaying means for displaying a distribution position determined by the position determining means and the medicine specifying means, wherein the assignment condition includes a maximum package number having a maximum package number that can be assigned to the tray, and wherein the position determining means is configured to sequentially count a package number of each of the prescription data received by the receiving means and to put an accumulated value of the counted package number as a maximum value not exceeding the maximum package number to determine the position of the medicine to be distributed to each of the measures of the tray.

2. The distributed medicine supplying device of claim 1, wherein the assignment condition further includes at least one of following conditions: an assignment per ward building; an assignment by a prescription number; an assignment by reception time; and a forced assignment; and
wherein the position determining means is configured to determine the prescription data to be assigned to the tray when one of two or more of the assignment conditions including the assignment by a maximum package number are satisfied.

3. A method of determining a position in which medicines are distributed to a plurality of measures defined in a tray, comprising:
receiving a prescription data;
reading a barcode on a packaging box for vials or medicines;
specifying a medicine based on the barcode with reference to a stored database;
determining a position of a medicine to be distributed to each of the measures of the tray according to an assignment condition based on the received prescription data; and
displaying a determined distribution position with respect to the specified medicine,
wherein the assignment condition includes a maximum package number having a maximum package number that can be assigned to the tray, and
wherein the step of determining the position of the medicine includes:
sequentially counting a package number of each of the received prescription data; and
putting an accumulated value of the counted package number as a maximum value not exceeding the maximum package number to determine the position of the medicine to be distributed to each of the measures of the tray.

4. The method of claim 3, wherein the assignment condition further includes at least one of following conditions: an assignment per ward building; an assignment by a prescription number; an assignment by reception time; and a forced assignment; and
wherein the step of determining the position of the medicine further includes determining the prescription data to be assigned to the tray when one of two or more of the assignment conditions including the assignment by a maximum package number are satisfied.

5. A medicine packaging device for sequentially supplying and packaging medicines accommodated in a plurality of measures defined in a tray, comprising:
a receiving means for receiving a prescription data;
a storing means for storing an assignment condition for a medicine to be accommodated in each of the measures of the tray;
a barcode reader;
a medicine specifying means for reading a barcode on a packaging box for vials or medicines by means of the barcode reader and specifying a medicine with reference to the storing means;
a position determining means for determining a position of the medicine to be distributed to each of the measures of the tray in accordance with the assignment condition stored in the storing means based on the prescription data sequentially received by the receiving means; and
a displaying means for displaying a distribution position determined by the position determining means and the medicine specifying means,
wherein the assignment condition includes a maximum package number having a maximum package number that can be assigned to the tray, and
wherein the position determining means is configured to sequentially count a package number of each of the prescription data received by the receiving means and to put an accumulated value of the counted package number as a maximum value not exceeding the maximum package number to determine the position of the medicine to be distributed to each of the measures of the tray.

6. The medicine packaging device of claim 5, wherein the assignment condition further includes at least one of following conditions: an assignment per ward building; an assignment by a prescription number; an assignment by reception time; and a forced assignment; and
wherein the position determining means is configured to determine the prescription data to be assigned to the tray when one of two or more of the assignment conditions including the assignment by a maximum package number are satisfied.

7. A distributed medicine supplying device for sequentially supplying medicines accommodated in a plurality of measures defined in a tray, comprising:
a receiving means for receiving a prescription data;
a storing means for storing an assignment condition for a medicine accommodated in each of the measures of the tray;
a position determining means for determining a position of the medicine to be distributed to each of the measures of the tray in accordance with the assignment condition stored in the storing means based on the prescription data sequentially received by the receiving means;
a displaying means for displaying a distribution position determined by the position determining means; and
a means for photographing the tray in entirety to verify the medicine accommodated in each of the measures,
wherein the assignment condition includes a maximum package number having a maximum package number that can be assigned to the tray, and
wherein the position determining means is configured to sequentially count a package number of each of the prescription data received by the receiving means and to put an accumulated value of the counted package number as a maximum value not exceeding the maximum package number to determine the position of the medicine to be distributed to each of the measures of the tray.

8. The distributed medicine supplying device of claim 7, wherein the assignment condition further includes at least one of following conditions: an assignment per ward building; an assignment by a prescription number; an assignment by reception time; and a forced assignment; and
wherein the position determining means is configured to determine the prescription data to be assigned to the tray when one of two or more of the assignment conditions including the assignment by a maximum package number are satisfied.

* * * * *